United States Patent [19]

Choudhary et al.

[11] Patent Number: 5,763,725
[45] Date of Patent: Jun. 9, 1998

[54] PROCESS FOR THE PRODUCTION OF ETHYLENE BY NON-CATALYTIC OXIDATIVE CRACKING OF ETHANE OR ETHANE RICH $C_2$-$C_4$ PARAFFINS

[75] Inventors: Vasant Ramchandra Choudhary; Amarjeet Munshiram Rajput; Shafeek Abdul Rashid Mulla, all of Pune, India

[73] Assignee: Council of Scientific & Industrial Research, New Delhi, India

[21] Appl. No.: 933,109

[22] Filed: Sep. 18, 1997

Related U.S. Application Data

[63] Continuation of Ser. No. 495,776, Jun. 27, 1995, abandoned.
[51] Int. Cl.⁶ .......................................... C07C 4/04
[52] U.S. Cl. .................... 585/652; 585/648; 585/621; 585/910
[58] Field of Search .................... 585/648, 652, 585/621, 910

[56] References Cited

U.S. PATENT DOCUMENTS

| | | | |
|---|---|---|---|
| 4,172,857 | 10/1979 | Pavilon | 585/635 |
| 4,426,278 | 1/1984 | Kosters | 585/652 |
| 4,599,478 | 7/1986 | Kamisaka et al. | 585/648 |
| 5,306,845 | 4/1994 | Choudhary et al. | 585/315 |

*Primary Examiner*—Walter D. Griffin
*Attorney, Agent, or Firm*—Pennie & Edmonds LLP

[57] ABSTRACT

An improved process for the production of ethylene by non-catalytic oxidative cracking of ethane or ethane rich $C_2$–$C_4$ paraffins with high conversion, selectivity and productivity, operating in a most energy efficient and safe manner requiring little or no external energy, in an empty tubular reactor, wherein the exothermic oxidative conversion of ethane or ethane rich $C_2$–$C_4$ paraffins is coupled with the endothermic hydrocarbon cracking reactions by carrying out both the exothermic and endothermic reactions simultaneously in the reactor so that the heat produced in the exothermic reactions is used instantly in the endothermic reactions and thereby making the overall process mildly exothermic, near thermo-neutral or mildly endothermic, which comprises passing a preheated gaseous feed comprising of ethane or ethane rich $C_2$–$C_4$ paraffins, oxygen and steam through an empty tubular reactor operated at the effective temperature, pressure, space velocity and hydrocarbon/$O_2$ and hydrocarbon/steam mole ratios in the feed, is provided.

18 Claims, No Drawings

PROCESS FOR THE PRODUCTION OF ETHYLENE BY NON-CATALYTIC OXIDATIVE CRACKING OF ETHANE OR ETHANE RICH $C_2$-$C_4$ PARAFFINS

This is a continuation of application Ser. No. 08/495,776, filed Jun. 27, 1995, now abandoned.

FIELD OF THE INVENTION

This invention relates to an improved process for the production of ethylene by non-catalytic oxidative cracking of ethane or ethane rich $C_2$-$C_4$ paraffins. This invention particularly relates to production of ethylene by non-catalytic oxidative cracking of ethane or ethane rich $C_2$-$C_4$ paraffins in a most safe and energy efficient manner by allowing the endothermic hydrocarbon cracking reactions to occur simultaneously with the exothermic hydrocarbon oxidative conversion reactions in an empty tubular reactor.

The process of this invention could be used for the production of ethylene from ethane or ethane rich $C_2$-$C_4$ paraffins.

BACKGROUND OF THE INVENTION

At present, ethylene, which is a keystone to the petrochemicals, from ethane or light paraffins ($C_2$-$C_4$ paraffins) is produced commercially by a well established process based on the thermal cracking of ethane or $C_2$-$C_4$ paraffins at 750°–1000° C. (L. Kniel, O. Winter and K. Stork in Chemical Industries, Vol. 2 "Ethylene: Key-stone to the Petrochemical Industry", Marcel Dekkor, Inc., New York and Basel). The cracking process is highly endothermic and hence highly energy intensive and also involves extensive coke formation. Typical results given in the above reference indicate that at 50% and 60% conversion of ethane, 83.3% and 80.0% selectivity for ethylene, respectively, could be obtained by the thermal cracking of ethane. The ethylene and other olefins produced in the cracking process and the unreacted paraffins are separated from the product stream by the well known cryogenic separation method involving liquification and fractionation of hydrocarbons.

The processes for production of ethylene, based on thermal cracking of light paraffins have following limitations: (1) They are highly endothermic and hence require a large amount of energy for the cracking of paraffins. (2) They involve extensive coke deposition inside the pyrolysis reactor tubes, thus causing increase in pressure drop and hence there are frequent break-downs for removing the coke from the pyrolysis reactor tubes. 3) The life of the pyrolysis reactor tubes is low because of their high temperature operation; the temperature at external surface of the tubes is about 200° C. higher than the temperature inside the tubes.

In an earlier German patent (Ger. Offen 2, 645, 424, 28 Apr. 1977); Kurtz and Samalley have described a process for the manufacture of ethylene by oxidative dehydrogenation of ethane in presence of chlorine and air, using an axial jet reactor. In this process, chlorine and air were mixed and fed to a nickel axial jet reactor and ethane was added to provide an essentially uniform introduction in the reaction zone. At an autothermal cracking temperature of 960° C., a 78.8% yield of ethylene was achieved with a conversion of 88.8%. This process is not commercially feasible because of the requirement of chlorine in large or stoichiometric quantities and the formation of HCl, which is highly corrosive and hence hazardous, as a coproduct.

Catalytic processes based on oxidative dehydrogenation of ethane or light paraffins for the production of ethylene are also known in the prior art. A number of catalysts containing low melting compounds such as alkali metal compounds, metal halides and other low melting metal oxides are known for the oxidative dehydrogenation of ethane or lower alkanes [Ref. Eastman and Kolts, U.S. Pat. No. 4,310,717 (1982); Eastman, U.S. Pat. No. 4,368,346 (1983); Eastman and Kimble, U.S. Pat. No. 4,450,313 (1985); Kimble, U.S. Pat. No. 4,476,344 (1984); Eastman et.al., U.S. Pat. No. 4,497, 971 (1985); Jpn. Kokai Tokyo Koho JP 61,282,322 (1986); Kolts and Guillory, Eur. Pat. Appl. EP 205,765 (1986)]. Because of the presence of the low melting or volatile component, these catalysts are deactivated during the process due to the loss of active components from the catalyst by evaporation at hot spots and/or due to the catalyst sintering. The catalysts are also deactivated due to coke deposition on their surface during the process. Since, these processes are exothermic, their operation is hazardous.

The present energy crisis and/or high energy cost, and also the environmental pollution problems have created a great need for developing a process for the production of ethylene by non-catalytic oxidative cracking of ethane or ethane rich $C_2$-$C_4$ paraffins, which requires little (i.e. much smaller than that required for the thermal cracking process) or no external energy, operates in a most energy efficient manner and with high conversion, selectivity and productivity but without coke formation and also has absolutely no hazards (i.e. very safe operation). This invention is, therefore, made with the following objects so that most of the drawbacks or limitations of the earlier processes could be overcome.

SUMMARY OF THE INVENTION

1. Accordingly the main object of this invention is to provide a process for the production of ethylene from ethane or ethane rich $C_2$-$C_4$ paraffins by non-catalytic oxidative cracking of ethane or ethane rich $C_2$-$C_4$ paraffins in the presence of steam and limited oxygen so that their endothermic thermal cracking and exothermic oxidative conversion reactions, described later, occur simultaneously.

2. Another important object of this invention is to provide a non-catalytic process for the production of ethylene from ethane or ethane rich $C_2$-$C_4$ paraffins, which requires little (i.e. much smaller than that required for the thermal cracking process) or no external energy and also operates in a most energy efficient manner without any hazards (i.e. with a very safe process operation) through coupling of the exothermic oxidative hydrocarbon conversion reactions with the endothermic hydrocarbon cracking or pyrolysis reactions.

3. Yet another object of this invention is to provide a process for the production of ethylene from ethane or ethane rich $C_2$-$C_4$ paraffins by their simultaneous oxidative conversion and thermal cracking, which operates with high conversion, selectivity and productivity without deposition of coke on the reactor walls for a long period.

DETAILED DESCRIPTION OF THE INVENTION

This invention provides a non-catalytic process for the production of ethylene by oxidative cracking of ethane or ethane rich $C_2$-$C_4$ paraffins with high conversion, selectivity and productivity, operating in most energy efficient and safe manner, in an empty tubular reactor. The process comprises of passing continuously a gaseous feed comprising of ethane or ethane rich $C_2$-$C_4$ paraffins, oxygen and steam, preheated at 200° C.–600° C. through an empty tubular reactor at the temperature 700° C.–1000° C., pressure 0.5–5 atm, space velocity 100–100,000 $h^{-1}$ and mole ratios of hydrocarbon to oxygen and to steam in the feed 2.5–75 and 0.1–10, respectively.

Accordingly, this invention provides an improved process for the production of ethylene from ethane or ethane rich $C_2$–$C_4$ paraffins which comprises:

a) mixing of oxygen or air with enriched oxygen and ethane or ethane rich $C_2$–$C_4$ paraffins at ambient temperature (0°–50° C.).

b) preheating steam and the mixture of oxygen or air enriched with oxygen and ethane or ethane rich $C_2$–$C_4$ paraffins to a temperature between about 200° C. and about 650° C., c) admixing said preheated steam with said preheated mixture of oxygen or air enriched with oxygen and ethane or ethane rich $C_2$–$C_4$ paraffins, d) passing continuously the resulting admixture feed through an empty tubular reactor, while maintaining the mole ratio of hydrocarbon to oxygen and to steam in said admixture feed between about 2.5 and about 75 and between about 0.1 and about 10, respectively, a gas hourly space velocity of said admixture feed between about 100 $h^{-1}$ and about 100,000 $h^{-1}$, a reaction temperature between about 700° C. and about 1000° C. and a pressure between about 0.5 atm and about 5.0 atm and cooling and separating the components of effluent product gases by known methods and recycling the unconverted reactants.

In the process of the present invention, the preferred reaction temperature is between about 750° C, and about 900° C.; the preferred pressure ranges from about 1 atm to about 4 atm; the preferred mole ratio of hydrocarbon to oxygen and to steam in the feed ranges from about 4 to about 20 and about 0.3 to about 3, respectively; and the preferred gas hourly space velocity of the feed ranges from about 500 $h^{-1}$ to about 20,000 $h^{-1}$.

In the process of the present invention the products formed are ethylene with smaller amounts of higher olefins (mainly propylene and butylenes with much smaller amounts of $C_{5+}$ olefins), methane, hydrogen, carbon monoxide, carbon dioxide and water. The gaseous product stream comprises of ethylene, propylene, butylenes, traces of $C_{5+}$ olefins, methane, $H_2$, CO, $CO_2$, $H_2O$ and unconverted ethane or $C_2$–$C_4$ paraffins and oxygen or air components.

The feed used in the process of the present invention comprises of ethane or ethane rich $C_2$–$C_4$ paraffins, oxygen or air enriched with oxygen, and steam. The hydrocarbon components of the feed and oxygen are reactants but steam is a feed diluent and acts as an indirect reactant for the gasification of the carbon formed in the process under oxygen deficient conditions or by thermal cracking or pyrolysis of hydrocarbons. The presence of steam in the feed has two beneficial effects: one, the formation of coke and tar-like product in the process are avoided and second, the severity of the exothermic hydrocarbon oxidation reactions is reduced due to the feed dilution. The steam in the product stream can be easily separated simply by its condensation. The oxygen in the feed plays following important roles in the process. Because the presence of oxygen in the feed, not only the total rate of ethane conversion due to both the thermal cracking and oxidative conversion of ethane but also the rate of thermal cracking ethane is increased and hence the productivity of ethylene in the process of this invention is higher than that in the thermal cracking process. Further, because of the oxidation of coke precursors i. e. hydrogen deficient or highly unsaturated hydrocarbon species, formed in the conversion of the ethane or lower paraffins, by the oxygen, the coke formation in the process of this invention is avoided. The preheating of the feed gases can be effected by exchanging heat between the hot reactor effluent product gas stream and the feed gases by any known conventional methods.

Following non-catalytic exothermic and endothermic reactions occur in the process of present invention.

Exothermic Reactions a) Oxidative dehydrogenation of ethane or $C_2$–$C_4$ paraffins $$C_2H_6 + 0.5O_2 \rightarrow C_2H_4 + H_2O + 25.1 \text{ Kcal} \quad (1)$$

$H_r = -25.1$ Kcal·$mol^{-1}$ of $C_2H_6$ or $$C_nH_{2n+2} + 0.5O_2 \rightarrow C_nH_{2n} + H_2O + \text{heat} \quad (2)$$

b) Combustion of ethane or $C_2$–$C_4$ paraffins, which are highly exothermic reactions $$C_2H_6 + 3.5O_2 \rightarrow 2CO_2 + 3H_2O + 341.5 \text{ Kcal} \quad (3)$$

$H_r = -341.5$ Kcal·$mol^{-1}$ of ethane $$C_2H_6 + 2.5O_2 \rightarrow 2CO + 3H_2O + 206.6 \text{ Kcal} \quad (4)$$

$H_r = -206.6$ Kcal·$mol^{-1}$ of ethane or $$C_2\text{–}C_4 \text{ paraffins} + \text{Oxygen} \rightarrow CO, CO_2 \text{ and } H_2O + \text{heat} \quad (5)$$

c) Oxidation of hydrogen to water, which is also highly exothermic $$H_2 + 0.5O_2 \rightarrow H_2O + 59.4 \text{ Kcal} \quad (6)$$

$H_r = -59.4$ Kcal·$mol^{-1}$ of $H_2$

Endothermic Reactions

Thermal cracking or non-oxidative cracking or pyrolysis of ethane or $C_2$–$C_4$ paraffins.

$$C_2H_6 \rightarrow C_2H_4 + H_2 - 34.18 \text{ Kcal} \quad (7)$$

$H_r = +34.18$ Kcal·$mol^{-1}$ of ethane or $$C_2\text{–}C_4 \text{ alkanes} \rightarrow C_2H_4 \text{ and } C_3\text{–}C_4 \text{ olefins} + CH_4 + H_2 - \text{heat} \quad (8)$$

Wherein, $H_r$ = heat of reaction.

In the process of the present invention, since the above exothermic and endothermic reactions are occurring simultaneously, the heat produced in the exothermic reactions is used instantly for the endothermic reactions, thus making the process operation most energy efficient and safe. Since the thermal hydrocarbon cracking reactions have high activation energy, their reaction rate increases very fast with the increase in the temperature. The coupling of the exothermic and endothermic reactions, as described above, leads to an establishment of a sort of a buffer action for the reaction temperature in the process thus restricting the temperature rise and, therefore, an occurrence of run-away reaction condition during the operation of the process is totally eliminated. Because of the coupling of the exothermic and endothermic reactions occurring simultaneously, the process of this invention can be made mildly exothermic, near thermo-neutral or mildly endothermic by manipulating the process conditions.

The process can be operated in an empty non-adiabatic tubular reactor, containing single or multiple parallel tubes, without any serious problems for removing heat from the reactor, when the process is mildly exothermic or providing energy to the reactor, when the process is mildly endothermic, thus requiring no or little (i.e, much smaller than that required for the thermal cracking process)external energy, respectively.

The present invention is described with respect to the following examples illustrating the process of this invention for the simultaneous exothermic oxidative conversion of ethane and endothermic thermal cracking of ethane, which is a representative of $C_2$–$C_4$ paraffins, in a most safe and energy efficient manner. These examples are provided for illustrative purposes only and are not to be construed as limitations on the invention.

Definition of Terms Used in the Examples

Total conversion of reactant (%) mol % of the reactant converted to all the products.

Conversion of a reactant to a particular product=mol % of the reactant converted to the particular product.

Selectivity for a particular product (%)=100×[Conversion of reactant to the product (%)]/[Total conversion of reactant (%)].

Gas hourly space velocity, GHSV=Volume of gaseous reactant mixture, measured at 0° C. and 1 atm pressure, passed through an unit volume of reactor per hour.

All the ratios of reactants or products are mole ratios.

The net heat of reactions, $H_r$, in the overall process is defined as follows:

Net heat of reactions, $H_r=[H_f]_{products}-[H_f]_{reactants}$, wherein, $[H_f]_{products}$ and $[H_f]_{reactants}$ are the heat of formation of products and reactants, respectively. The negative value of the net heat of reactions indicate that the overall process is exothermic and the positive value of the net heat of reactions indicate that the overall process is endothermic.

EXAMPLE—1

This example illustrates the process of this invention for the production of ethylene by non-catalytic oxidative cracking of ethane, which is a representative of $C_2$–$C_4$ paraffins, in the presence of oxygen and steam at different process conditions.

The process is carried out in a continuous flow empty tubular reactor made up of quartz, having a volume of 5.2 cm$^3$, by passing through the reactor a feed comprising of ethane, oxygen and steam at different reaction conditions. The feed was preheated at 300° C. before passing through the reactor. The reactor was kept in an electrically heated tubular furnace. The reaction temperature was measured by Chromel-Alumel thermocouple located axially in the center of the reactor. The reactor effluent gases were cooled at about 0° C. to condense the water from them, using a coiled condenser immersed in ice-water slurry, and then analyzed for the products and unconverted reactants by an on-line gas chromatograph.

The process performance is evaluated at the following process conditions:

Feed: A mixture of ethane, oxygen and steam $C_2H_6/O_2$ mole ratio in feed: varied from 5 to 7.9

$C_2H_6/H_2O$ mole ratio in feed: varied from 0.3 to 10

Gas hourly space velocity (GHSV): varied from 1005 to 14,600 h$^{-1}$

Pressure: 1.1 atm.

Reaction temperature: varied from 750° to 850° C.

The results obtained at the different process conditions are presented in Tables 1–3. No coke formation is observed in the process.

The net heat of reactions in the process is quite small with positive or negative sign, indicating that the process at the corresponding reaction conditions is mildly endothermic or mildly exothermic, respectively. This example illustrates that the process of this invention occurs in a most energy efficient and safe manner and also the process can be made mildly exothermic, near thermo-neutral or mildly endothermic by manipulating the process conditions. This example also illustrates that for the process of present invention, either there is no requirement of external energy, particularly when the net heat of reaction, $H_r$ is negative ( i.e. when the present process is mildly exothermic) or there is a requirement of much lower energy than that required for the thermal cracking of ethane, which is endothermic with net heat of reaction, $H_r$=34.2 kcal·mol$^{-1}$. The net heat of reaction in the process of present invention is much lower than that of the thermal cracking process.

TABLE 1

Results on the non-catalytic simultaneous cracking and oxidative dehydrogenation of ethane to ethylene.

| | Run No. | | | | |
|---|---|---|---|---|---|
| | 1 | 2 | 3 | 4 | 5 |
| Process conditions | | | | | |
| Reaction temp. (°C.) : | 850 | 850 | 800 | 850 | 800 |
| GHSV (h$^{-1}$) : | 1980 | 1960 | 1960 | 1970 | 1970 |
| $C_2H_6/O_2$ mole ratio : | 6.4 | 6.3 | 6.3 | 6.4 | 6.4 |
| $C_2H_6/H_2O$ mole ratio : | 0.3 | 0.46 | 0.46 | 0.93 | 0.93 |
| Conversion (%) of | | | | | |
| $C_2H_6$ : | 91.2 | 90.1 | 79.7 | 89.2 | 69.9 |
| $O_2$ : | 98.1 | 97.4 | 95.7 | 98.8 | 98.2 |
| Selectivity (%) for | | | | | |
| $C_2H_4$ : | 79.5 | 73.5 | 74.1 | 77.4 | 79.2 |
| $C_3H_6$ : | 0.94 | 0.91 | 1.4 | 1.3 | 1.7 |
| $C_3H_8$ : | 0.15 | 0.17 | 0.4 | 0.2 | 0.3 |
| $C_4H_8$ : | 3.74 | 3.15 | 3.0 | 3.8 | 2.9 |
| $C_4H_{10}$ : | — | — | — | — | — |
| $CH_4$ : | 8.0 | 11.2 | 8.1 | 9.1 | 7.5 |
| CO : | 7.6 | 10.8 | 12.7 | 8.0 | 8.2 |
| $CO_2$ : | 0.16 | 0.3 | 0.4 | 0.2 | 0.2 |
| Net heat of reaction, | | | | | |
| $H_r$ (Kcal.mole$^{-1}$ of $C_2H_6$) : | +13.98 | +4.49 | +2.58 | +1.81 | −3.44 |

TABLE 2

Results on the non-catalytic simultaneous cracking and oxidative dehydrogenation of ethane to ethylene.

| | Run No. | | | | |
|---|---|---|---|---|---|
| | 1 | 2 | 3 | 4 | 5 |
| Process conditions | | | | | |
| Reaction temp. (°C.) : | 800 | 800 | 750 | 850 | 750 |
| GHSV (h$^{-1}$) : | 1980 | 1960 | 1960 | 1950 | 1970 |
| $C_2H_6/O_2$ mole ratio : | 6.4 | 7.9 | 7.9 | 5.0 | 6.4 |
| $C_2H_6/H_2O$ mole ratio : | 0.3 | 0.95 | 0.95 | 0.88 | 0.93 |
| Conversion (%) of | | | | | |
| $C_2H_6$ : | 76.5 | 71.2 | 53.5 | 87.6 | 52.6 |
| $O_2$ : | 97.7 | 96.3 | 96.3 | 98.9 | 94.5 |
| Selectivity (%) for | | | | | |
| $C_2H_4$ : | 81.9 | 80.2 | 79.0 | 76.7 | 78.8 |
| $C_3H_6$ : | 1.3 | 1.8 | 2.1 | 1.6 | 2.2 |
| $C_3H_8$ : | 0.25 | 0.42 | 1.0 | 0.16 | 0.89 |

TABLE 2-continued

Results on the non-catalytic simultaneous cracking and oxidative dehydrogenation of ethane to ethylene.

| | Run No. | | | | |
|---|---|---|---|---|---|
| | 1 | 2 | 3 | 4 | 5 |
| $C_4H_8$ | 2.60 | 3.10 | 1.35 | 4.0 | 1.3 |
| $C_4H_{10}$ | — | — | 1.6 | — | 1.3 |
| $CH_4$ | 6.6 | 7.2 | 6.2 | 9.2 | 6.7 |
| CO | 7.2 | 7.1 | 8.6 | 8.2 | 8.6 |
| $CO_2$ | 0.17 | 0.14 | 0.17 | 0.21 | 0.23 |
| Net heat of reaction, | | | | | |
| $H_r$ (Kcal.mole$^{-1}$ of $C_2H_6$) | +12.95 | +7.45 | +0.69 | −2.97 | −7.74 |

TABLE 3

Results on the non-catalytic simultaneous cracking and oxidative dehydrogenation of ethane to ethylene.

| | Run No. | | | | |
|---|---|---|---|---|---|
| | 1 | 2 | 3 | 4 | 5 |
| Process conditions | | | | | |
| Reaction temp. (°C.) | 850 | 800 | 800 | 800 | 750 |
| GHSV (h$^{-1}$) | 1005 | 2030 | 14530 | 14890 | 14600 |
| $C_2H_6/O_2$ mole ratio | 6.4 | 7.9 | 7.0 | 5.0 | 6.4 |
| $C_2H_6/H_2O$ mole ratio | 0.9 | 10.0 | 0.93 | 0.93 | 0.93 |
| Conversion (%) of | | | | | |
| $C_2H_6$ | 90.5 | 67.7 | 53.5 | 65.4 | 40.9 |
| $O_2$ | 96.5 | 98.6 | 94.6 | 94.5 | 74.4 |
| Selectivity (%) for | | | | | |
| $C_2H_4$ | 77.5 | 78.5 | 81.1 | 78.1 | 78.1 |
| $C_3H_6$ | 1.14 | 2.4 | 2.4 | 1.84 | 2.7 |
| $C_3H_8$ | 0.18 | 0.47 | 0.71 | 0.86 | 1.4 |
| $C_4H_8$ | 4.0 | 3.30 | 2.0 | 1.3 | 0.83 |
| $C_4H_{10}$ | — | — | 1.0 | 0.8 | 2.93 |
| $CH_4$ | 10.6 | 8.1 | 5.3 | 7.1 | 5.6 |
| CO | 6.4 | 7.0 | 7.4 | 9.9 | 8.2 |
| $CO_2$ | 0.14 | 0.2 | 0.13 | 0.2 | 0.17 |
| Net heat of reaction, | | | | | |
| $H_r$ (Kcal.mole$^{-1}$ of $C_2H_6$) | +13.22 | +6.08 | +4.83 | +3.59 | −6.92 |

EXAMPLE—2

This example illustrates the process of the present invention for the production of ethylene by non-catalytic oxidative cracking of ethane in the presence of oxygen enriched air and steam at different process conditions.

The process is carried out in the reactor and by the procedure same as that described in Example—1 except that oxygen enriched air instead of pure oxygen is used in the feed and feed comprising of ethane, oxygen, $N_2$ and steam was preheated at 500° C. before passing through the reactor. The process performance was evaluated at following process conditions.

Feed: A mixture of ethane, oxygen, $N_2$ and steam
$C_2H_6/O_2$ mole ratio in feed: varied from 5 to 8
$C_2H_6/H_2O$ mole ratio in feed: varied from 0.3 to 10
$O_2/N_2$ mole ratio in feed: 0.6

Gas hourly space velocity (GHSV): varied from 1960 to 14,890 h$^{-1}$

Pressure: 1.1 atm.

Reaction temperature: varied from 700° to 90° C.

The results obtain at the different process conditions are given in Table—4. There was no coke deposition on the reactor walls.

This example also illustrates that the process of this invention can be made mildly exothermic or mildly endothermic by manipulating the process conditions. The observed net heat of the reaction is much lower than that of the thermal cracking of ethane and hence there is large energy saving.

TABLE 4

Results on the non-catalytic simultaneous cracking and oxidative dehydrogenation of ethane to ethylene.

| | Run No. | | | | | |
|---|---|---|---|---|---|---|
| | 1 | 2 | 3 | 4 | 5 | 6 |
| Process conditions | | | | | | |
| Reaction temp. (°C.) | 900 | 850 | 800 | 850 | 750 | 700 |
| GHSV (h$^{-1}$) | 14600 | 7340 | 7450 | 14890 | 2030 | 1950 |
| $C_2H_6/O_2$ mole ratio | 6.4 | 6.4 | 8.0 | 5.0 | 7.9 | 7.9 |
| $C_2H_6/H_2O$ mole ratio | 0.93 | 0.3 | 1.0 | 0.93 | 10.0 | 0.95 |
| Conversion (%) of | | | | | | |
| $C_2H_6$ | 89.8 | 85.2 | 59.3 | 70.1 | 48.4 | 41.1 |
| $O_2$ | 98.8 | 97.1 | 96.1 | 97.8 | 98.3 | 90.7 |
| Selectivity (%) for | | | | | | |
| $C_2H_4$ | 79.3 | 81.0 | 83.5 | 78.0 | 75.7 | 75.1 |
| $C_3H_6$ | 1.1 | 1.0 | 1.7 | 1.6 | 3.0 | 2.5 |
| $C_3H_8$ | 0.4 | 0.3 | 0.5 | 0.3 | 1.1 | 1.8 |
| $C_4H_8$ | 3.3 | 2.9 | 1.9 | 3.0 | 1.7 | 0.9 |
| $C_4H_{10}$ | — | — | 0.7 | — | 2.2 | 3.8 |
| $CH_4$ | 8.3 | 7.0 | 5.6 | 7.1 | 7.5 | 7.1 |
| CO | 7.6 | 7.8 | 6.0 | 9.8 | 8.6 | 9.1 |
| $CO_2$ | 0.12 | 0.2 | 0.1 | 0.2 | 0.2 | 0.2 |
| Net heat of reaction, | | | | | | |
| $H_r$ (Kcal.mole$^{-1}$ of $C_2H_6$) | +13.7 | +15.1 | +11.5 | +5.2 | −4.8 | −4.2 |

EXAMPLE—3

This example illustrates that in the presence of limited $O_2$ in the feed of the process of present invention, not only the rate of total conversion of ethane but also the rate of thermal cracking of ethane is much higher than that observed in the absence of $O_2$ The ethane conversion reactions in the presence of $O_2$ and in the absence of $O_2$ were carried out in the reactor same as that described in Example 1 by passing through it a feed comprising of ethane and steam with or without $O_2$ and measuring the rate of ethane conversion at different temperatures and space velocities. The steam/ethane mole ratio in the feed was 1.0. A comparison of the rate of thermal cracking of ethane ($r_{EC}$) in the presence of $O_2$, at different $C_2H_6/O_2$ mole ratios in feed, with the rate of thermal cracking of ethane ($r_{EC}$) in the absence of $O_2$ at different temperatures and space velocities is presented in Table 5.

TABLE 5

Comparison of rate of thermal cracking of ethane ($r_{EC}$) in presence and absence of oxygen(steam/ethane mole ratio in feed = 1.0).

| Temp. (°C.) | Space velocity (h$^{-1}$) | C$_2$H$_6$/O$_2$ mole ratio in feed | In presence of O$_2$ | | In absence of O$_2$ |
|---|---|---|---|---|---|
| | | | $r_T^a$ (mol.m$^{-3}$.s$^{-1}$) | $r_{EC}$ (mol.m$^{-3}$.s$^{-1}$) | $r_{EC}$ (mol.m$^{-3}$.s$^{-1}$) |
| 700 | 3700 | 7.1 | 7.8 | 4.5 | 0.9 |
| 750 | 3700 | 7.1 | 10.4 | 7.3 | 4.3 |
| 700 | 7380 | 10.0 | 12.5 | 6.8 | 1.1 |
| 750 | 7380 | 10.0 | 18.4 | 13.1 | 7.2 |
| 800 | 7380 | 10.0 | 25.7 | 20.8 | 16.7 |
| 700 | 11050 | 7.1 | 20.2 | 7.1 | 1.4 |
| 750 | 11050 | 7.1 | 27.5 | 17.0 | 5.3 |
| 800 | 11050 | 7.1 | 38.9 | 28.3 | 19.6 |
| 700 | 7400 | 5.0 | 16.2 | 6.3 | 1.1 |
| 750 | 7400 | 5.0 | 20.3 | 11.4 | 7.2 |

$^a r_T$ = rate of ethane conversion by both the thermal cracking and oxidative conversion of ethane in the presence of O$_2$.

The main advantages of this invention or major improvements achieved by this invention over the earlier processes for the production of ethylene from ethane or C$_2$–C$_4$ paraffins are as follows 1. In the process of this invention, because of the simultaneous occurrence of the endothermic hydrocarbon cracking reactions and the exothermic oxidative hydrocarbon conversion reactions, the heat produced in the exothermic reactions is used instantly in the endothermic reactions. The coupling of the exothermic reactions with the endothermic ones has imparted following outstanding features to the process of the present invention:

a. The process is operated in a most energy efficient manner with large energy saving, achieving high conversion of paraffins with high selectivity for ethylene and other lower (C$_3$ and C$_4$) olefins and also the process is operated at higher space velocity on lower contact time, thus increasing the productivity or space time—yield of ethylene.

b. The process is operated in a very safe manner with no possibility of reaction run-away conditions.

c. The process can be made mildly exothermic, near thermo-neutral or mildly endothermic by manipulating the process conditions. The net heat of reaction in this process is much lower than that in the earlier thermal cracking process and hence requirement of external energy in the process of this invention is much lower than that required in the earlier thermal cracking processes.

d. The process can be operated in a non-adiabatic empty tubular reactor without any serious problems for removing heat from the reactor, when the process is mildly exothermic or for providing energy to the reactor, when the process is mildly endothermic, thus requiring no or much smaller external energy than that required for the thermal cracking process, respectively.

e. Because of the presence of oxygen, not only the rate of total conversion of ethane but also the rate thermal cracking of ethane, which is occurring simultaneously with the oxidative conversion of ethane, is enhanced, hence the productivity of ethylene in the process of this invention is higher than that in the earlier thermal cracking process operating in the absence of oxygen.

Because of the presence of oxygen and steam in the feed, there is no coke deposition on the reactor walls in the process of this invention. Whereas, in the earlier thermal cracking process, there is an extensive coke deposition in the pyrolysis reactor tubes, causing increase in pressure drop across the reactor and ultimatly process break-down for the coke removal. Also because of the coke deposition, the life of the reactor tubes in the thermal cracking process is low. These limitations of the earlier thermal cracking process are also overcome in the process of present invention.

2. The process of this invention has following advantages over the earlier process based on the oxidative dehydrogenation of ethane in the presence of chlorine and air, described in Ger. Offen 2, 645, 624. The process of this invention does not involve the formation of HCl, which is high corrosive and hence highly hazardous.

3. The process of this invention has also number of advantages over the earlier process based on the catalytic oxidative dehydrogenation of ethane to ethylene.

a) The process of this invention does not involve a use of catalyst and therefore there are no problems of catalyst deactivation due to sintering or loss of active components or coke deposition. The process operating cost is also reduced as no catalyst is required.

b) The process of this invention can be made thermo-neutral, mildly exothermic or mildly endothermic by controlling the simultaneously occurring exothermic oxidative conversion and endothermic thermal cracking reactions; hence the process occur in a most energy efficient and safe manner and the operation of process is simple. Where as the catalytic oxidative dehydrogenation is exothermic and hence a hazardous process, not safe to operate.

c) The reactor design, process operation and process control for the catalytic oxidative dehydrogenation process are much more complicated because of its hazardous nature and catalyst deactivation and heat and mass transfer problems in the catalytic process, as compared to the non-catalytic process of this invention.

We claim:

1. A process for the production of ethylene by non-catalytic oxidative cracking of ethane or ethane rich C$_2$–C$_4$ paraffins involving the coupling of endothermic and exothermic reactions, which comprises:

a) mixing oxygen or oxygen enriched air with ethane or ethane rich C$_2$–C$_4$ paraffins at temperatures ranging from 0°–50° C.

b) separately preheating steam and the mixture formed in step a) to a temperature between about 200° C. and about 650° C.;

c) admixing the preheated steam with the preheated mixture formed in step a);

d) continuously passing the resulting admixture from step c) through an empty tubular reactor, while maintaining process conditions of (1) a mole ratio of hydrocarbon to oxygen and steam in the admixture at between about 2.5 and about 75 and between about 0.1 and about 10, respectively, (2) a gas hourly space velocity of the admixture between about 100 $h^{-1}$ and about 100,000 $h^{-1}$, (3) a reaction temperature between about 700° C. and about 1000° C., and (4) a pressure between about 0.5 atm and about 5.0 atm to thus provide coupling of endothermic and exothermic reactions;

e) cooling and separating the components of effluent product gases; and f) recycling unconverted reactants.

2. A process as claimed in claim 1 wherein the reaction temperature is maintained between about 750° C. and about 900° C.

3. A process as claimed in claim 1 wherein the pressure employed ranges from about 1.0 atm to about 4 atm.

4. A process as claimed in claim 1 wherein the mole ratio of hydrocarbon to oxygen and to steam in feed ranges from about 4 to about 20 and about 0.3 to about 3, respectively.

5. A process as claimed in claim 1 wherein the gas hourly space velocity of feed ranges from about 500 $h^{-1}$ to about 20,000 $h^{-1}$.

6. A process for the production of ethylene by non-catalytic oxidative cracking of ethane or ethane rich $C_2-C_4$ paraffins involving the coupling of endothermic and exothermic reactions, which comprises:

a) mixing oxygen or oxygen enriched air with ethane or ethane rich $C_2-C_4$ paraffins at temperatures ranging from 0°–50° C.;

b) separately preheating steam and the mixture formed in step a) to a temperature between about 200° C. and about 650° C.;

c) admixing the preheated steam with the preheated mixture while minimizing condensation of the steam, the steam being present in an amount which avoids formation of coke during the subsequent reaction;

d) continuously passing the resulting admixture from step c) through an empty tubular reactor, while maintaining process conditions of (1) a mole ratio of hydrocarbon to oxygen and steam in the admixture at between about 2.5 and about 75 and between about 0.1 and about 10, respectively, (2) a gas hourly space velocity of the admixture between about 100 $h^{-1}$ and about 100,000 $h^{-1}$, (3) a reaction temperature between about 700° C. and about 1000° C., and (4) a pressure between about 0.5 atm and about 5.0 atm to thus provide coupling of endothermic and exothermic reactions;

e) cooling and separating the components of effluent product gases; and f) recycling unconverted reactants.

7. A process as claimed in claim 6 wherein the reaction temperature is maintained between about 750° C. and about 900° C.

8. A process as claimed in claim 6 wherein the pressure employed ranges from about 1.0 atm to about 4 atm.

9. A process as claimed in claim 6 wherein the mole ratio of hydrocarbon to oxygen and to steam in feed ranges from about 4 to about 20 and about 0.3 to about 3, respectively.

10. A process as claimed in claim 6 wherein the gas hourly space velocity of feed ranges from about 500 $h^{-1}$ to about 20,000 $h^{-1}$.

11. The process of claim 1, wherein the reactions have a net thermochemistry within the range of slightly endothermic to slightly exothermic.

12. The process of claim 11, wherein the reactions are substantially net thermoneutral.

13. The process of claim 1, wherein the endothermic reaction is a hydrocarbon cracking reaction.

14. The process of claim 1, wherein the exothermic reaction is an oxidative hydrocarbon reaction.

15. The process of claim 6, wherein the reactions have a net thermochemistry within the range of slightly endothermic to slightly exothermic.

16. The process of claim 15, wherein the reactions are substantially net thermoneutral.

17. The process of claim 6, wherein the endothermic reaction is a hydrocarbon cracking reaction.

18. The process of claim 6, wherein the exothermic reaction is an oxidative hydrocarbon reaction.

* * * * *